US008851396B2

(12) United States Patent
Irvin

(10) Patent No.: US 8,851,396 B2
(45) Date of Patent: Oct. 7, 2014

(54) DUAL SCENT AIR FRESHENER WITH MANUAL COMBINER

(75) Inventor: Aaron Irvin, Salt Lake City, UT (US)

(73) Assignee: American Covers, Inc., Draper, UT (US)

( * ) Notice: Subject to any disclaimer, the term of this patent is extended or adjusted under 35 U.S.C. 154(b) by 597 days.

(21) Appl. No.: 12/693,543

(22) Filed: Jan. 26, 2010

(65) Prior Publication Data

US 2010/0187327 A1 Jul. 29, 2010

Related U.S. Application Data

(60) Provisional application No. 61/147,591, filed on Jan. 27, 2009.

(51) Int. Cl.
*A61L 9/04* (2006.01)
*A61L 9/12* (2006.01)
*B60H 3/00* (2006.01)

(52) U.S. Cl.
CPC .......... *A61L 9/127* (2013.01); *B60H 2003/0064* (2013.01); *B60H 3/0007* (2013.01); *A61L 9/125* (2013.01)
USPC .................. 239/49; 239/44; 239/58; 239/326

(58) Field of Classification Search
USPC .............. 239/44, 45, 47, 49, 50, 51.5, 57–59, 239/326
See application file for complete search history.

(56) References Cited

U.S. PATENT DOCUMENTS

| 369,878 | A | 9/1887 | Palmer |
|---|---|---|---|
| 1,171,737 | A | 2/1916 | Madigan |
| 2,244,944 | A | 6/1941 | Furlonge |
| 3,239,145 | A | 3/1966 | Aurelio |
| 3,552,632 | A | 1/1971 | Wilson |
| 3,847,305 | A | 11/1974 | Tobin |
| D246,986 | S | 1/1978 | Costello |
| 4,084,079 | A | 4/1978 | Costello |
| 4,149,675 | A | 4/1979 | Van Breen et al. |
| 4,280,649 | A | 7/1981 | Montealegre |
| 4,382,548 | A | 5/1983 | van der Heijden |

(Continued)

FOREIGN PATENT DOCUMENTS

| CA | 2077251 | 5/1993 |
|---|---|---|
| WO | WO 98/46284 | 10/1998 |
| WO | WO 2006/010282 | 6/2006 |

OTHER PUBLICATIONS

U.S. Appl. No. 12/623,007, filed Nov. 20, 2009, Alan J. Wheatley; office action issued Jul. 29, 2011.

(Continued)

*Primary Examiner* — Jason Boeckmann
(74) *Attorney, Agent, or Firm* — Thorpe North & Western LLP

(57) ABSTRACT

An air freshener includes a pair of wicks extending from a pair of reservoirs configured to contain different scents. A hood is sized and shaped to essentially cover only one of the at least two wicks and movable with respect to the wicks between a first scent position in which the hood essentially covers a second of the at least two wicks, a second scent position in which the hood essentially covers a first of the at least two wicks, and a plurality of combined scent positions in which the hood partially covers both of the at least two wicks.

16 Claims, 4 Drawing Sheets

(56) References Cited

U.S. PATENT DOCUMENTS

| | | | |
|---|---|---|---|
| 4,391,781 | A | 7/1983 | van Lit |
| 4,549,693 | A | 10/1985 | Barlics |
| 4,660,764 | A * | 4/1987 | Joyaux et al. .................. 239/44 |
| 4,808,347 | A | 2/1989 | Dawn |
| 4,840,773 | A | 6/1989 | Wade |
| 4,849,606 | A | 7/1989 | Martens et al. |
| 4,950,542 | A | 8/1990 | Barker |
| 4,967,988 | A | 11/1990 | Nguyen |
| 5,034,222 | A | 7/1991 | Kellett et al. |
| D319,781 | S | 9/1991 | Halm et al. |
| 5,050,798 | A | 9/1991 | Sullivan |
| 5,114,625 | A | 5/1992 | Gibson |
| 5,120,583 | A | 6/1992 | Garcia |
| 5,180,107 | A | 1/1993 | Lindauer |
| D334,975 | S | 4/1993 | Bunce |
| 5,208,027 | A | 5/1993 | Weder et al. |
| 5,234,162 | A | 8/1993 | Sullivan |
| 5,240,487 | A | 8/1993 | Kung |
| D349,157 | S | 7/1994 | Rymer |
| D350,192 | S | 8/1994 | Patel et al. |
| 5,407,642 | A | 4/1995 | Lord |
| 5,422,078 | A | 6/1995 | Colon |
| D367,924 | S | 3/1996 | Patel et al. |
| 5,520,921 | A | 5/1996 | Chalifoux |
| D373,626 | S | 9/1996 | Dente et al. |
| D375,350 | S | 11/1996 | Patel et al. |
| 5,595,194 | A | 1/1997 | Talbot |
| 5,651,522 | A | 7/1997 | Davis et al. |
| 5,704,832 | A | 1/1998 | Borrell |
| D392,032 | S | 3/1998 | Zaragoza et al. |
| 5,725,152 | A | 3/1998 | Akyu |
| D400,662 | S | 11/1998 | Davis |
| 5,860,552 | A | 1/1999 | Culhane et al. |
| 5,899,382 | A | 5/1999 | Hayes et al. |
| D410,540 | S | 6/1999 | Pinchuk |
| 5,988,520 | A | 11/1999 | Bitner |
| D424,677 | S | 5/2000 | Chen |
| 6,059,156 | A | 5/2000 | Lehtinen |
| 6,102,660 | A | 8/2000 | Lee |
| 6,123,935 | A | 9/2000 | Wefler et al. |
| D432,222 | S | 10/2000 | Rymer et al. |
| D435,694 | S | 12/2000 | Lebherz |
| D437,041 | S | 1/2001 | Eisenbraun |
| 6,197,263 | B1 | 3/2001 | Blount |
| D441,441 | S | 5/2001 | Upson |
| 6,325,475 | B1 | 12/2001 | Hayes et al. |
| D454,190 | S | 3/2002 | Trocola |
| 6,357,260 | B1 | 3/2002 | Lutz |
| 6,391,398 | B1 | 5/2002 | Pesu et al. |
| 6,514,467 | B1 | 2/2003 | Bulsink et al. |
| D472,968 | S | 4/2003 | Christianson |
| D491,257 | S | 6/2004 | Picken |
| D496,720 | S | 9/2004 | Dudley |
| 6,830,733 | B2 | 12/2004 | Stanley, III |
| 6,885,811 | B2 | 4/2005 | He et al. |
| D504,943 | S | 5/2005 | Dudley |
| 6,976,637 | B2 | 12/2005 | Massimo |
| D515,192 | S | 2/2006 | Smith et al. |
| 7,055,764 | B1 | 6/2006 | Martinez et al. |
| 7,070,172 | B2 | 7/2006 | Fabraga et al. |
| D535,376 | S | 1/2007 | Michaels et al. |
| D544,080 | S | 6/2007 | Carlson |
| D544,084 | S | 6/2007 | Michaels et al. |
| D544,594 | S | 6/2007 | Zobele |
| D544,953 | S | 6/2007 | Kee |
| D548,317 | S | 8/2007 | Newton et al. |
| D550,345 | S | 9/2007 | Weggelaar |
| D551,333 | S | 9/2007 | Wu |
| D554,746 | S | 11/2007 | Davis et al. |
| D565,162 | S | 3/2008 | Carlson |
| 7,344,123 | B2 | 3/2008 | Pankhurst et al. |
| D565,715 | S | 4/2008 | Wu |
| 7,389,943 | B2 * | 6/2008 | Jaworski .................. 239/102.2 |
| D573,706 | S | 7/2008 | Zlotnik et al. |
| D574,941 | S | 8/2008 | Weggelaar |
| 7,441,360 | B2 | 10/2008 | Christianson et al. |
| D580,039 | S | 11/2008 | Zlotnik et al. |
| D585,129 | S | 1/2009 | Huang |
| D591,415 | S | 4/2009 | Wu |
| D593,670 | S | 6/2009 | Valentino et al. |
| 7,544,332 | B2 | 6/2009 | De Silva et al. |
| D597,645 | S | 8/2009 | Thompson |
| D598,531 | S | 8/2009 | Irvin |
| D604,825 | S | 11/2009 | Brandenburg |
| D607,983 | S | 1/2010 | Irvin |
| 7,651,666 | B2 | 1/2010 | Adair et al. |
| 7,670,566 | B2 | 3/2010 | Adair et al. |
| D614,277 | S | 4/2010 | Hsiao |
| D622,835 | S | 8/2010 | Mendheim |
| D629,881 | S | 12/2010 | Valentino et al. |
| D631,534 | S | 1/2011 | Kajizuka |
| D631,954 | S | 2/2011 | Bertassi et al. |
| D633,610 | S | 3/2011 | Wu |
| D637,275 | S | 5/2011 | Baraky |
| D640,781 | S | 6/2011 | Brandenburg |
| D642,668 | S | 8/2011 | Lablaine |
| D645,949 | S | 9/2011 | Brandenburg et al. |
| D647,186 | S | 10/2011 | Chan et al. |
| D649,237 | S | 11/2011 | Bilko et al. |
| D662,581 | S | 6/2012 | Savegnago |
| 8,197,761 | B1 | 6/2012 | Miller-Larry |
| D667,100 | S | 9/2012 | Hakim |
| 8,485,454 | B1 | 7/2013 | Irvin |
| 8,490,846 | B1 | 7/2013 | Wheatley |
| 2001/0051234 | A1 | 12/2001 | Ryan et al. |
| 2004/0197221 | A1 | 10/2004 | Stanley, III |
| 2004/0265164 | A1 | 12/2004 | Woo et al. |
| 2005/0084413 | A1 | 4/2005 | Stanley, III |
| 2005/0127538 | A1 | 6/2005 | Fabrega et al. |
| 2006/0043216 | A1 | 3/2006 | Robinson |
| 2006/0078477 | A1 | 4/2006 | Althouse et al. |
| 2006/0196964 | A1 | 9/2006 | Wheatley et al. |
| 2006/0279008 | A1 | 12/2006 | Jursich |
| 2007/0048173 | A1 * | 3/2007 | Keller et al. ...................... 422/5 |
| 2007/0160492 | A1 | 7/2007 | Spector |
| 2007/0231508 | A1 | 10/2007 | Fand et al. |
| 2007/0290064 | A1 * | 12/2007 | Majerowski et al. ............ 239/44 |
| 2008/0099576 | A1 | 5/2008 | Hart |
| 2008/0128925 | A1 | 6/2008 | Pankhurst et al. |
| 2008/0311315 | A1 | 12/2008 | Marlow |
| 2008/0311316 | A1 | 12/2008 | Marlow |
| 2009/0004420 | A1 | 1/2009 | Wheatley |
| 2009/0010813 | A1 | 1/2009 | Wang et al. |
| 2009/0072045 | A1 | 3/2009 | Wheatley et al. |
| 2009/0173799 | A1 * | 7/2009 | Litten-Brown et al. ........... 239/6 |
| 2010/0019059 | A1 * | 1/2010 | Bulsink et al. .................. 239/55 |
| 2010/0065654 | A1 | 3/2010 | Wheatley et al. |
| 2010/0288847 | A1 | 11/2010 | Gruenbacher et al. |
| 2011/0108632 | A1 | 5/2011 | Brandenburg et al. |

OTHER PUBLICATIONS

U.S. Appl. No. 29/394,683, filed Jun. 20, 2011, Alan J. Wheatley; notice of allowance issued Aug. 22, 2011.
U.S. Appl. No. 13/191,966, filed Jul. 27, 2011, Aaron Irvin.
U.S. Appl. No. 12/623,007, filed Nov. 20, 2009, Alan J. Wheatley; notice of allowance issued Nov. 28, 2012.
Scents & Sprays, www.scentsandsprays.com/ya . . . , Yankee Autumn Bounty Electric 2 Home Air Freshener, copyright 2001-2008 scentsandsprays.com, accessed Oct. 2, 2008, 1 page.
ecrater, www.ecrater.com/product.php? . . . , Yankee Candle Selects Two Scents Electric Fragrance Unit Macintosh/Home Sweet Home, accessed Oct. 2, 2008, 1 page.
Aromate E-News, Innovatio nin Novelty Fragrance, http://209.85.173.104/seasrch?q=cach . . . , accessed Oct. 8, 2008, 2 pages.
About.com Housekeeping, http://housekeeping.about.com/od/pr . . . affresh, Febreze Noticeables, accessed Oct. 2, 2008, 2 pages.
U.S. Appl. No. 29/378,112, filed Oct. 29, 2010, Nathaniel Finlay; Notice of Allowance issued Mar. 29, 2012.
U.S. Appl. No. 29/16,038, filed Oct. 29, 2010, Aaron Irvin; Notice of Allowance issued Apr. 27, 2012.
U.S. Appl. No. 29/415,358, filed Mar. 9, 2012, Aaron Irvin; Notice of Allowance issued May 29, 2012.

(56) References Cited

OTHER PUBLICATIONS

U.S. Appl. No. 13/282,035, filed Oct. 26, 2011, Nathaniel Finlay; office action dated Jul. 17, 2013.
U.S. Appl. No. 12/979,795, filed Dec. 28, 2010, Aaron Irvin; office action dated Oct. 18, 2013.
U.S. Appl. No. 13/940,074, filed Jul. 11, 2013, Alan J. Wheatley; office action dated Nov. 20, 2013.
U.S. Appl. No. 12/915,924, filed Oct. 29, 2010, Nathaniel Finlay; notice of allowance dated Nov. 22, 2013.
U.S. Appl. No. 13/282,035, filed Oct. 26, 2011, Nathaniel Finlay; notice of allowance dated Nov. 26, 2013.
U.S. Appl. No. 13/281,890, filed Oct. 26, 2011; Aaron Irvin; notice of allowance dated Dec. 10, 2013.
U.S. Appl. No. 12/979,763, filed Dec. 28, 2010, Aaron Irvin notice of allowance dated Apr. 15, 2013.
U.S. Appl. No. 13/282,035, filed Oct. 26, 2011, Nathaniel Finlay, office action dated Apr. 17, 2013.
U.S. Appl. No. 12/987,662, filed Jan. 10, 2011, Alan J. Wheatley; notice of allowance dated Jun. 7, 2013.
U.S. Appl. No. 12/979,690, filed Dec. 28, 2010, Alan J. Wheatley; notice of allowance dated Jun. 10, 2013.
U.S. Appl. No. 12/979,601, filed Dec. 28, 2010, Alan J. Wheatley; notice of allowance dated Jun. 10, 2013.
U.S. Appl. No. 29/435,391, filed Oct. 23, 2012, Aaron Irvin, notice of allowance dated Jun. 18, 2013.
U.S. Appl. No. 29/435,389, filed Oct. 23, 2012, Aaron Irvin; notice of allowance dated Mar. 1, 2013.
U.S. Appl. No. 12/979,690, filed Dec. 28, 2010, Alan J. Wheatley; office action dated Mar. 1, 2013.
U.S. Appl. No. 12/987,662, filed Jan. 10, 2011, Alan J. Wheatley; office action dated Mar. 21, 2013.
U.S. Appl. No. 12/979,601, filed Dec. 28, 2010, Alan J. Wheatley; office action dated Mar. 1, 2013.
U.S. Appl. No. 13/009,574, filed Jan. 19, 2011, Alan J. Wheatley notice of allowance dated Apr. 3, 2013.
U.S. Appl. No. 13/359,726, filed Jan. 27, 2012, Aaron Irvin; office action dated Apr. 5, 2013.
U.S. Appl. No. 12/979,813, filed Dec. 28, 2010, Aaron Irvin; office action dated Sep. 14, 2012.
U.S. Appl. No. 12/979,795, filed Dec. 28, 2010, Aaron Irvin; office action dated Sep. 13, 2012.
U.S. Appl. No. 12/979,763, filed Dec. 28, 2010, Aaron Irvin; office action dated Dec. 14, 2012.
U.S. Appl. No. 13/009,574, filed Jan. 19, 2011, Alan J. Wheatley; office action dated Jan. 11, 2013.
U.S. Appl. No. 12/979,795, filed Dec. 28, 2010, Aaron Irvin; office action dated Jan. 28, 2013.
U.S. Appl. No. 12/979,813, filed Dec. 28, 2010, Aaron Irvin; office action dated Jan. 31, 2013.
U.S. Appl. No. 12/915,983; filed Oct. 29, 2010; Alan J. Wheatley; notice of allowance dated Feb. 20, 2013.
U.S. Appl. No. 13/191,966, filed Jul. 27, 2011, Aaron Irvin; office action dated Jun. 11, 2014.

* cited by examiner

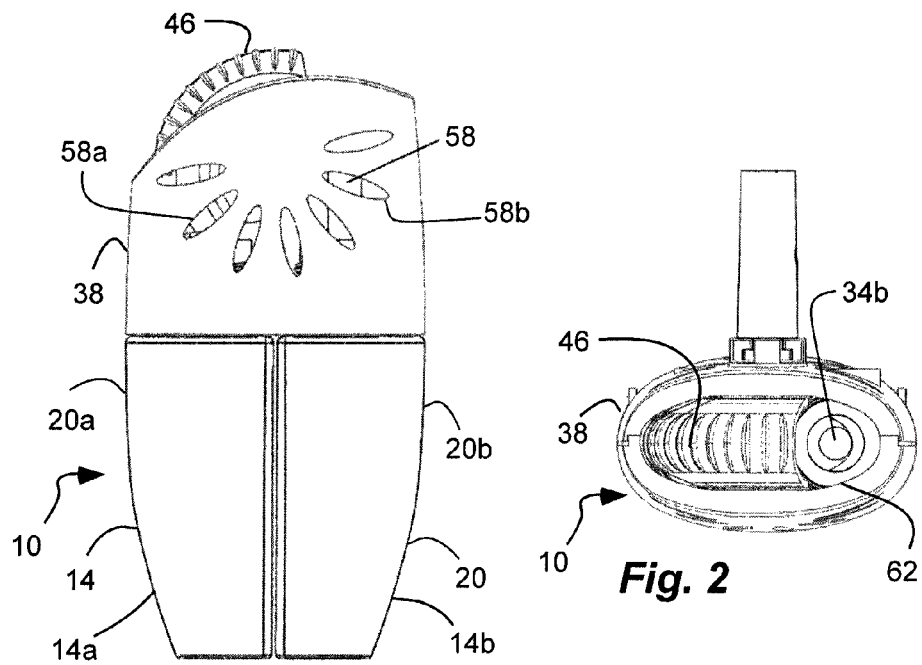
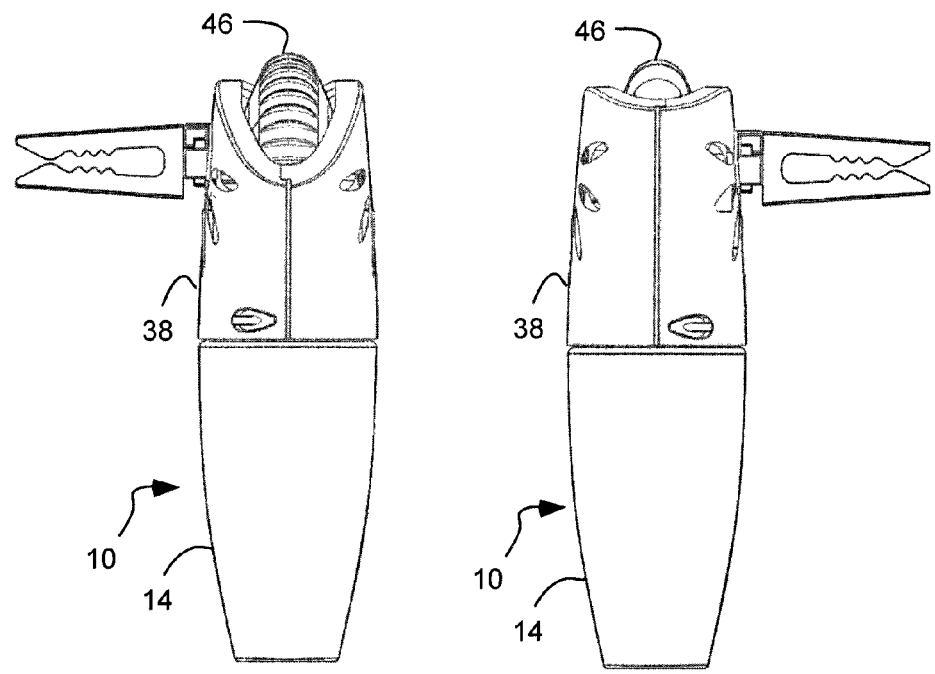

DUAL SCENT AIR FRESHENER WITH MANUAL COMBINER

PRIORITY CLAIM

Priority is claimed to U.S. Provisional Patent Application Ser. No. 61/147,591, filed Jan. 27, 2009, which is hereby incorporated herein by reference in its entirety.

RELATED APPLICATIONS

This is related to U.S. Design patent application Nos. 29/331,515 and 29/331,512, filed Jan. 27, 2009, now U.S. Pat. Nos. D598,531 and D607,983; which are hereby incorporated herein by reference in their entirety.

BACKGROUND

1. Field of the Invention

The present invention relates generally to air fresheners. More particularly, the present invention relates to a dual air freshener with two different scents manually combinable together.

2. Related Art

Various types of air fresheners have been developed. Some air fresheners provide two scents that can be combined together. For example, see U.S. Pat. No. 7,055,764; U.S. 2008/0128925; U.S. Pat. No. 7,344,123; U.S. Pat. No. 5,050,798; W) 2006/010282; The Aromate Double Fresh (No. HF905); Yankee Candle Selects Two Scents Electric Fragrance Unit; and Fabreze Noticeables. Some air fresheners require electricity to power fans.

SUMMARY OF THE INVENTION

It has been recognized that it would be advantageous to develop an air freshener that allows two complimentary scents to be combined by a user. In addition, it has been recognized that it would be advantageous to develop an air freshener with selective or controllable scent release.

The invention provides a pair of wicks extending from a pair of reservoirs configured to contain different scents. A hood is sized and shaped to essentially cover only one of the at least two wicks and movable with respect to the wicks between a first scent position in which the hood essentially covers a second of the at least two wicks, a second scent position in which the hood essentially covers a first of the at least two wicks, and a plurality of combined scent positions in which the hood partially covers both of the at least two wicks.

The invention also provides an air freshener with a reservoir configured to contain a scented liquid. A wick is disposed in the reservoir and extends therefrom. A hood is sized and shaped to essentially cover the wick and movable with respect to the wick between a first scent position in which the hood essentially covers the wick, a second scent position in which the hood exposes the wick, and a plurality of variable scent positions in which the hood partially covers the wick.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 1 is a front view of an air freshener in accordance with an embodiment of the present invention;

FIG. 2 is a top view of the air freshener of FIG. 1;

FIGS. 3a and 3b are side views of the air freshener of FIG. 1;

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

As illustrated in FIG. 1-5c, a dual scent air freshener, indicated generally at 10, in an example implementation in accordance with the invention is shown. Such an air freshener can be used in a variety of applications, including for example, in a vehicle interior. The air freshener can include two different scents or fragrances, such as complimentary fragrances or scents, that can be released individually, or in combination in various proportions determined by a user.

Figure 4A:
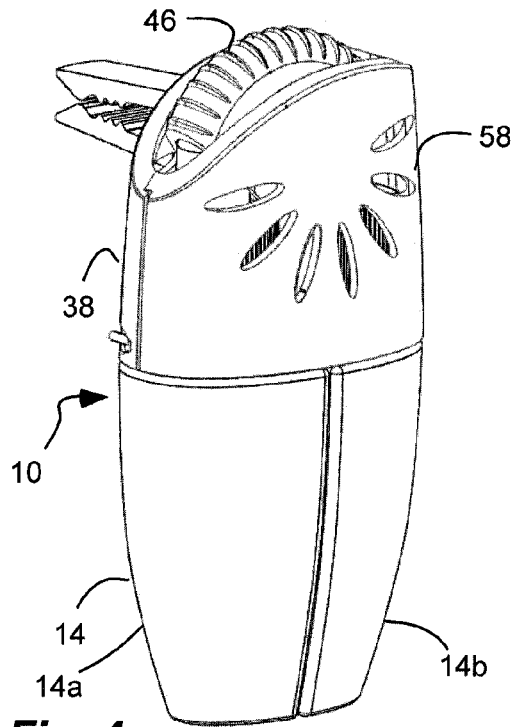
FIG. 4a is a perspective view of the air freshener of FIG. 1.
Figure 4B:
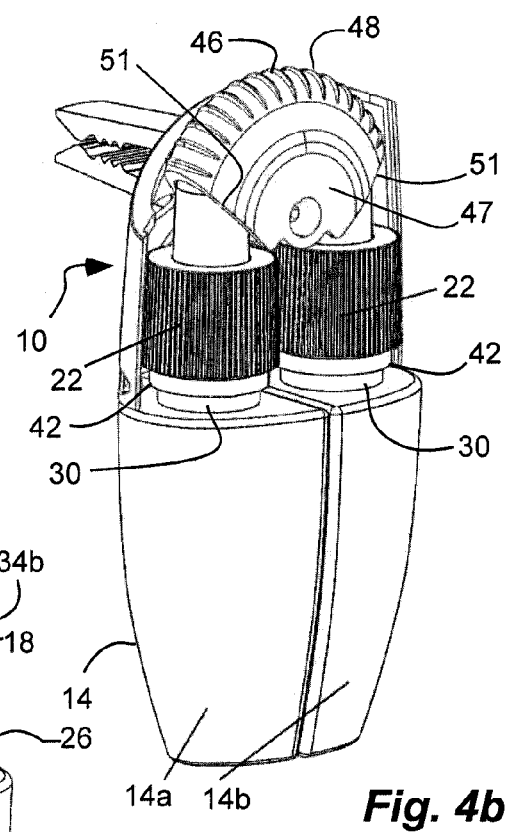
FIG. 4b is a perspective view of the air freshener of FIG. 1 shown with a portion of the housing removed and showing an un-used configuration.
Figure 4C:
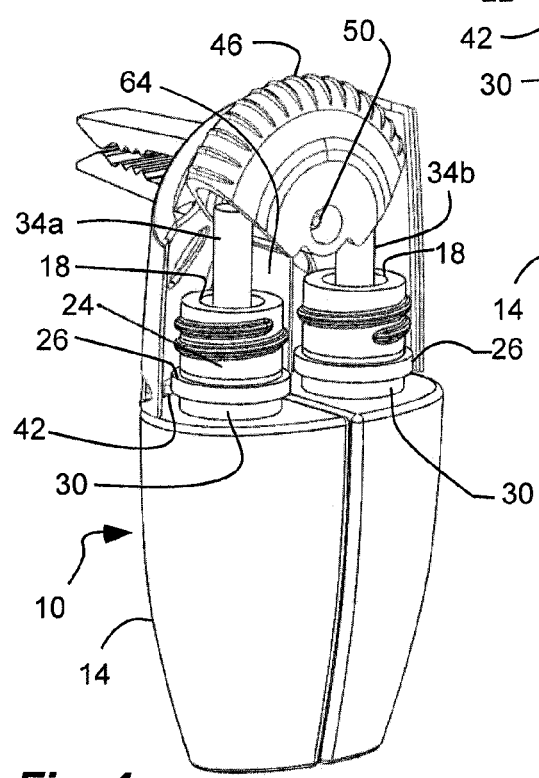
FIG. 4c is a perspective view of the air freshener of FIG. 1 shown with a portion of the housing removed and with the caps removed and showing an in-use configuration.

The air freshener can include at least two reservoirs 14 that contain different scented liquids, such as scented oil. The reservoirs 14 can include separate matching reservoirs 14a and 14b that can be abutted or disposed adjacent one another to form the general appearance of a single container with a continuous shape. The reservoirs 14 can be formed by at least two containers, vials or vessels 20 including one 20a corresponding to one vessel 14a and another 20b corresponding to the other vessel 14b. The reservoirs 14 or vessels 20 can include an opening 18 in a top end that that is configured to receive a removable cap 22 (FIG. 4b). The cap 22 can be threaded onto a threaded connection formed on the top of the reservoir. A stem 24 can extend from each vessel 14 or reservoir 20 with the 18 formed through the stem. The stem can have threads to receive the removable cap 22. In addition, each reservoir can have an annular flange or ring 26 disposed around the opening on the stem 24, and defining an annular groove 30 disposed between the flange and the reservoir. The reservoir can be made of plastic or glass, or the like.

A wick 34a and 34b is disposed in each reservoir 14a and 14b, respectively, and extends through the opening 18 and essentially to a bottom of the reservoir. The wicks can be formed of a fibrous material and can cause the scented oil to wick or climb through the opening, thus exposing the scented oil to the air. The caps 22 can include an elongated recess to accommodate the wicks. The caps can be disposed over the wicks and can seal the reservoirs prior to use. To use the air freshener, the caps are removed exposing the wicks.

A housing or collar 38 can be disposed over a top of the reservoir and the wicks and the caps. The housing can have an opening in a bottom through which the vessels 14 or reservoirs 20 extend. The vessels or reservoirs can be flush with the housing with the stems and wicks contained in the housing. The housing can include a pair of housings or halves that removably join together to enclose the wicks and caps, but can be separated to remove the caps. The pair of housings can have a snap fit or interference fit that hold them together. The housing 38 can have one or more tabs or lips 42 (FIG. 4c) disposed at the bottom thereof that extend into the groove 30 of the reservoirs to secure the housing to the reservoirs, and to secure the reservoirs together.

Figure 5A:
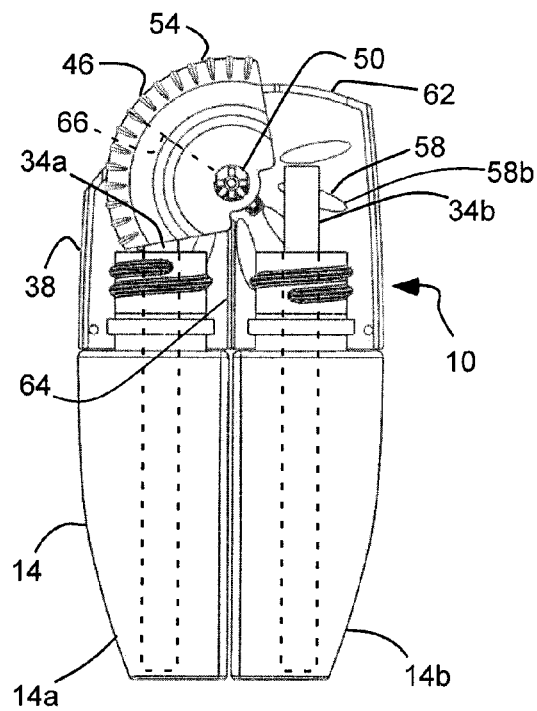
FIGS. 5a-c are front views of the air freshener of FIG. 1 shown with a portion of the housing removed and showing the hood in various different configurations.
Figure 5B:
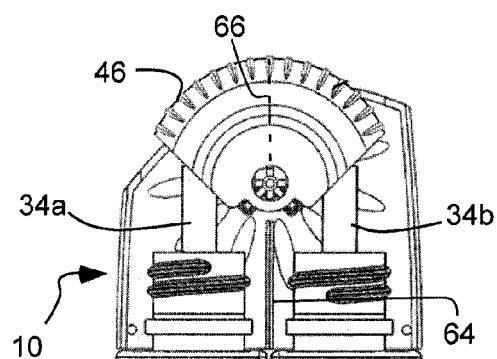
Figure 5C:
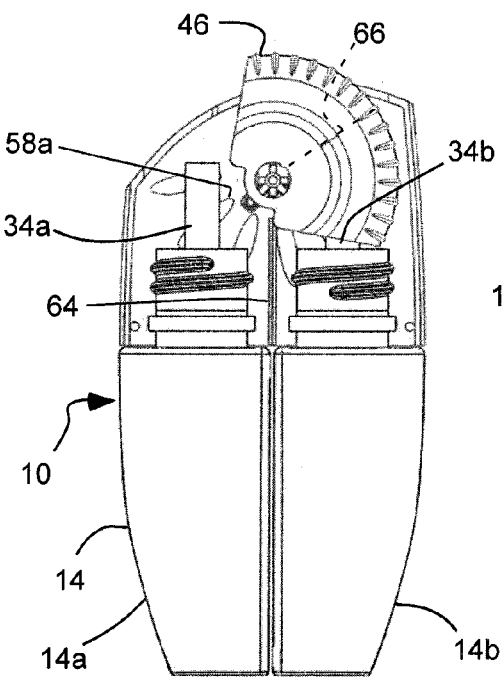

A hood 46 is positioned to selectively cover one of the wicks entirely or a select portion of both wicks. Thus, the hood can be sized and shaped to essentially cover only one of the at least two wicks. The hood is movable with respect to the wicks between a first scent position, as shown in FIG. 5a, in which the hood essentially covers a second 34a of the at least two wicks; a second scent position, as shown in FIG. 5c, in which the hood essentially covers a first 34b of the at least two wicks; and a plurality of combined scent positions, represented by FIG. 5b, in which the hood partially covers both of the at least two wicks. In the first scent position, shown in FIG. 5a, the first wick 34a is exposed releasing a first scent from the first reservoir 14b. Similarly, in the second scent position, shown in FIG. 5c, the second wick 34a is exposed releasing a second scent from the second reservoir 14a. In FIG. 5b, the hood 46 is selectively positioned to expose both wicks and release both scents from both reservoirs. It will be appreciated that the hood 46 can be selectively positioned with respect to both wicks to selectively expose the wicks and selectively release the scents.

The hood 46 can be pivotally about a pivot axis 50 between the two wicks. The hood can include a bore to receive a pivot post extending from the housing, or from one or both housing halves. Alternatively, the hood can include one or more pivot posts extending into one or more bores of the housing. The hood can have the shape of a hollow, partial disc or a hollow, partial pie shape, such as substantially a quarter disc or pie shape. The shape of the hood can be s U-shape or arch swept about the pivot substantially 90 degrees, give or take 5-10 degrees. The hood 46 can have opposite lateral walls 47 spaced apart and oriented perpendicularly to the pivot. A partial edge wall 48 is disposed between the lateral walls spaced from the pivot and partially circumscribing the pivot. The partial edge wall can be curved. The hood has a pair of openings 51 each disposed on a different side of the pivot which each receive a different one of the wicks therethrough and into the hollow as the hood moves or pivots. The openings are defined between the pivot, the lateral walls and the edge wall. Thus, as the hood pivots, the wicks are received into the hollow. A portion of the hood, such as a portion of the edge wall and lateral walls, can extend from the housing, such as through an upper opening in the housing, and can have a finger engaging surface or finger dial 54 for engagement by a user. The housing can at least partially surrounding the hood and a top portion of the at least two wicks extending from the at least two reservoirs. A plurality of air flow openings 58 can be formed in the housing, such as at least two openings 58a and 58b each on a different side of the housing and corresponding to different wicks, to define an air flow path through the housing and past the top portions of the at least two wicks. The hood can be sized and shaped to block the air flow path past one of the at least two wicks and to span the plurality of air flow opens adjacent the one of the at least two wicks. In addition, a top opening 62 can be formed in the housing above the at least two wicks defining an air flow path above the top portions of the at least two wicks. The hood can be sized and shaped to block the air flow path above one of the at least two wicks and to span the top opening above the one of the at least two wicks. The housing can include a wall 64 separating the wicks. The wall can extend vertically from the opening in the bottom to the pivot. In addition, the hood can include a wall 66 separating the hood into two portions. The walls can essentially or substantially separate the two wicks and the at least two openings 58a and 58b. Thus, when the hood is in the first scent position, as shown in FIG. 5a, the hood essentially covers the second 34a of the at least two wicks and the opening 58a; while exposing the first 34b of the at least two wicks and the opening 58b (and the top opening 62 above the wick). When the hood is in the second scent position, as shown in FIG. 5c, the hood essentially covers the first 34b of the at least two wicks and the opening 58b; while exposing the second 34a of the at least two wicks and the opening 58a (and the top opening 62 above the wick).

A top of the collar or housing 38 can be inclined with one side at a different elevation than the other. Thus, the top opening can be disposed closer to one wick than to the other. The inclined top can facilitate engagement with the hood. In addition, the top of the collar or housing can be curved or arcuate to facilitate engagement the hood.

A clip can be affixed to the housing to allow the air freshener to be affixed to another device, such as the grill of an air vent, such as a vehicle air vent.

Figure 6:
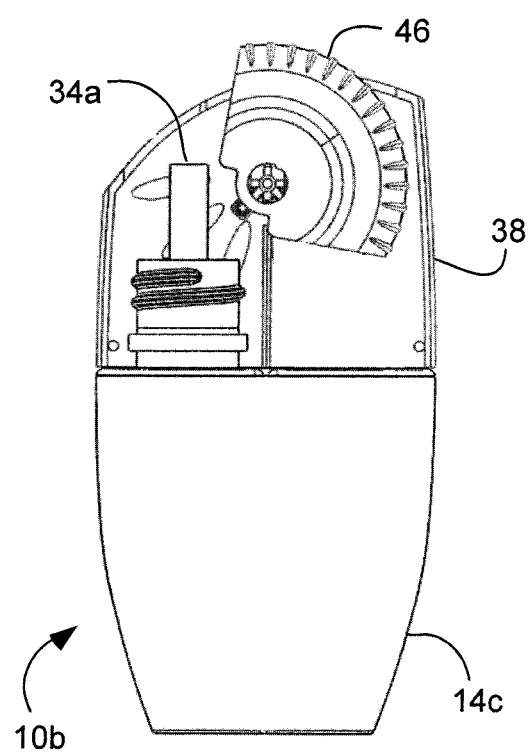
FIG. 6 is a front view of another air freshener in accordance with another embodiment of the present invention.

Referring to FIG. 6, another air freshener 10b is shown that is similar in most respects to that described above, but configured to be a single scent air freshener with a single reservoir 14c and the a single wick 34a, with the hood 46 selectively movable over the wick to adjust the strength of the scent or amount of the scent release. The hood can have a first scent position in which the hood essentially covers the wick, a second scent position in which the hood exposes the wick, and a plurality of variable scent positions in which the hood partially covers the wick.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:
1. A dual scent air freshener device, comprising:
 a) at least two reservoirs configured to contain different scented liquids;
 b) at least two wicks, each wick disposed in a different one of the at least two reservoirs and extending therefrom;
 c) a hood with a hollow and selectively movable with respect to the at least two wicks between a first scent position in which the hood receives a second of the at least two wicks into the hollow, a second scent position in which the hood receives a first of the at least two wicks into the hollow, and a plurality of combined scent positions in which the hood partially receives both of the at least two wicks into the hollow;
 d) the hood being pivotally connected about a pivot axis perpendicular to the at least two wicks;
 e) at least two openings through a housing, each on a different side of the housing corresponding to a different one of the at least two wicks;
 f) a wall in the housing separating the at least two wicks; and
 g) a wall disposed in the hood separating the hood into two portions, the walls of the housing and the hood essentially separating the at least two wicks and the at least to openings.
2. A device in accordance with claim 1, wherein the hood is shaped as a hollow, quarter disc or pie shape.

3. A device in accordance with claim 2, wherein the hood has opposite lateral walls perpendicular to the pivot and a partial edge wall between the lateral walls and partially circumscribing the pivot.

4. A device in accordance with claim 3, wherein the hood has a pair of openings, each on a different side of the pivot to receive a different one of the at least two wicks, each opening defined between the pivot, the lateral walls, and the edge wall.

5. A device in accordance with claim 1, further comprising:
the housing partially surrounding the hood and a top portion of the at least two wicks extending from the at least two reservoirs; and
a portion of the hood extending from the housing and having a finger engaging surface for engagement by a user.

6. A device in accordance with claim 1, further comprising:
the housing partially surrounding the hood and a top portion of the at least two wicks extending from the at least two reservoirs;
the pair at least two openings comprising a plurality of air flow openings in the housing defining an air flow path through the housing and past the top portions of the at least two wicks; and
the hood being sized and shaped to block the air flow path past one of the at least two wicks and to span the plurality of air flow opens adjacent the one of the at least two wicks.

7. A device in accordance with claim 1, further comprising:
the housing partially surrounding the hood and a top portion of the at least two wicks extending from the at least two reservoirs;
a top opening in the housing above the at least two wicks defining an air flow path above the top portions of the at least two wicks; and
the hood being sized and shaped to block the air flow path above one of the at least two wicks and to span the top opening above the one of the at least two wicks.

8. A device in accordance with claim 1, wherein the hood is a U-shape or arch swept about a pivot for substantially 90 degrees with opposite lateral walls spaced apart and oriented perpendicularly to the pivot and with an end wall deposed between the lateral walls and spaced from the pivot and partially circumscribing the pivot.

9. A device in accordance with claim 1, wherein the hood has a hollow and pivots about a pivot disposed between the wicks, and has opposite openings with the wicks received through the openings and into a hollow of the hood as the hood pivots.

10. A dual scent air freshener device, comprising:
a) at least two reservoirs coupled together adjacent one another and configured to contain different scented liquids;
b) at least two wicks, each wick disposed in a different one of the at least two reservoirs and extending therefrom;
c) a collar extending around the at least two wicks at a top of the at least two reservoirs;
d) a top opening in a top of the collar;
e) a pivoting hood pivotally disposed in the collar, the hood shaped as a hollow, quarter disc or pie shape with opposite lateral walls perpendicular to the pivot and a partial edge wall between the lateral walls and partially circumscribing the pivot, the hood pivotal with respect to the wicks between:
   i) a first scent position in which the hood receives a second of the at least two wicks into the hollow quarter disc or pie shape,
   ii) a second scent position in which the hood receives a first of the at least two wicks into the quarter disc or pie shape, and
   iii) a plurality of combined scent positions in which the hood partially receives both of the at least two wicks into the quarter disc or pie shape;
f) a portion of the hood extending through the top opening of the collar to define a finger dial engageable by a user to pivot the hood;
g) at least two openings through the collar, each on a different side of the collar corresponding to a different one of the at least two wicks;
i) a wall in the collar separating the at least two wicks; and
j) a wall disposed in the hood separating the hood into two portions, the walls of the collar and the hood essentially separating the at least two wicks and the at least to openings.

11. A device in accordance with claim 10, wherein the top of the collar is inclined with one side at a different elevation than another side.

12. A device in accordance with claim 10, wherein the hood is shaped as a hollow, quarter disc or pie shape.

13. A device in accordance with claim 12, wherein the hood has opposite lateral walls perpendicular to the pivot and a partial edge wall between the lateral walls and partially circumscribing the pivot.

14. A device in accordance with claim 13, wherein the hood has a pair of openings, each on a different side of the pivot to receive a different one of the at least two wicks, each opening defined between the pivot, the lateral walls, and the edge wall.

15. A device in accordance with claim 10, further comprising:
the pair at least two openings comprising a plurality of air flow openings in the collar defining an air flow path through the collar and past the top portions of the at least two wicks; and
the hood being sized and shaped to block the air flow path past one of the at least two wicks and to span the plurality of air flow opens adjacent the one of the at least two wicks.

16. A device in accordance with claim 10, further comprising:
a top opening in the collar above the at least two wicks defining an air flow path above the top portions of the at least two wicks; and
the hood being sized and shaped to block the air flow path above one of the at least two wicks and to span the top opening above the one of the at least two wicks.

* * * * *